United States Patent [19]

Takamoto et al.

[11] Patent Number: 5,151,590
[45] Date of Patent: Sep. 29, 1992

[54] PHOTOACOUSTIC CELL AND PHOTOACOUSTIC MEASURING DEVICE

[75] Inventors: Ryuichi Takamoto; Ryujiro Nanba; Masahiro Matsuoka, all of Yokohama; Tsuguo Sawada, Kodaira, all of Japan

[73] Assignee: Shiseido Company, Ltd., Tokyo, Japan

[21] Appl. No.: 748,320

[22] Filed: Aug. 20, 1991

[30] Foreign Application Priority Data

Aug. 20, 1990 [JP] Japan .................................. 2-218574
Aug. 1, 1991 [JP] Japan .................................. 3-193164

[51] Int. Cl.$^5$ .............................................. H01J 40/14
[52] U.S. Cl. .............................. 250/215; 250/227.11; 356/432
[58] Field of Search .............. 250/215, 227.11, 231.10; 356/432, 440; 359/149–151

[56] References Cited

U.S. PATENT DOCUMENTS

| | | | |
|---|---|---|---|
| 4,184,768 | 1/1980 | Murphy et al. | 356/217 |
| 4,533,252 | 8/1985 | Cahen | 356/432 |
| 4,860,224 | 8/1989 | Cashell et al. | 250/309 |
| 5,083,869 | 1/1992 | Nakata et al. | 356/432 |

FOREIGN PATENT DOCUMENTS 62-27215 2/1987 Japan .

OTHER PUBLICATIONS

Conception and Realization of a Photoacoustic detector for in Situ Spectroscopy, P. Poulet; J. Cambron, Journal of Photoacoustics, 1, 329–346 (1983).
Evaluation of drug penetration into skin by photoacoustic measurment, K. Kolmel; B. Sennhenn; K. Glese, J. Soe. Sosmet. Chem., (Sep./Oct.) 1986, 37, 375–385.

*Primary Examiner*—David C. Nelms
*Assistant Examiner*—Stephone Allen
*Attorney, Agent, or Firm*—Wegner, Cantor, Mueller & Player

[57] ABSTRACT

A photoacoustic cell, including a light guide having a fiber portion consisting of a bundle of a number of optical fibers and a covering portion by which the side surface of the fiber portion is covered, the covering portion of the light guide extending beyond the fiber portion in a manner that when a first end of the light guide is brought into contact with the surface of a material to be measured, a closed space is defined by the end surface of the fiber portion, by the inner wall of the covering portion, and by the surface of the material to be measured; a pipe having a first end that is open in the closed space and a second end that penetrates through the covering portion and is open toward the outside of the covering portion; and a microphone that is coupled to the second end of the pipe, and a photoacoustic measuring device including this photoacoustic cell.

12 Claims, 8 Drawing Sheets

PHOTOACOUSTIC CELL AND PHOTOACOUSTIC MEASURING DEVICE

BACKGROUND OF THE INVENTION

1. Field of the Invention

The present invention relates to a photoacoustic cell and to a photoacoustic measuring device constituted by using the same. More specifically, the invention relates to a photoacoustic cell and a photoacoustic measuring device that makes it possible to make in-vivo and in-situ measurement. Particularly, the invention relates to a photoacoustic cell and a photoacoustic measuring device that are expected to be used for a highly sensitive and highly precise measuring device required in the fields of measuring the amount of moisture in human skin and measuring the percutaneous absorption of medicines.

Furthermore, the invention relates to a photoacoustic cell and a photoacoustic measuring device which finds a wide range of applications using either the open type cell or the closed type cell and which, when a sample holder is optionally attached, can serve as a closed type photoacoustic measuring device, and which is small in size and is easy to use compared with the conventional closed type photoacoustic measuring devices and which is further expected to provide improved sensitivity and precision.

2. Description of the Related Art

A so-called non-destructive analytical method which qualitatively or quantitatively analyzes the materials to be measured without destroying them is becoming more important than ever before in the field of analysis of biological samples.

The conventional non-destructive analysis generally consists of irradiating a sample to be measured with light and measuring the reflected light or the transmitted light.

In the case of a biological sample having a rugged surface and strong scattering property, however, it is difficult with the conventional method to correctly measure the energy that is absorbed or reflected. This is because when the light absorption characteristics are to be measured, the light being irradiated decreases due not only to the absorption of light but also to the scattering of light and when the reflection characteristics are to be measured, correct measurement is hindered by the light scattered by the rugged surface.

In recent years, therefore, a photoacoustic method has been developed according to which the energy absorbed by a material being inspected is not measured as light but is measured as a pressure wave (sound wave) produced due to the generated heat. This has been applied to measuring the light absorption characteristics of materials having strong scattering properties such as biological samples since this method is little affected by the scattered light.

Here, the factor that dominates the amount of the generated heat is called the thermal diffusion length ($\mu$) and is expressed by the following formula.

$$\mu = (2k/\rho c \omega)^{\frac{1}{2}}$$

k: thermal conductivity of the material,
$\rho$: density of the material,
c: specific heat of the material,
$\omega$: angular modulation frequency of the irradiated light.

Therefore, when k, $\rho$, and c remain constant for a given material, the thermal diffusion length changes with a change in the frequency of the irradiated light, and the amount of the generated heat changes if there exists a material having thermally different properties in the region of the thermal diffusion length.

By changing the modulation frequency of the irradiated light, therefore, it becomes possible to effect the analysis in the direction of depth in the level of thermal diffusion length. Furthermore, since the intensity of signal varies in proportion to the intensity of the source of light, even those materials that absorb small amounts of light can be measured.

In the ordinary photoacoustic method, it is necessary to process the sample by cutting the sample so that it is placed and measured in a small closed type cell. In order to carry out in-vivo and in-situ analyses, the photoacoustic analytical method and apparatus using an open type cell have been reported according to which one surface of the cell is opened and an air-tight system for the material to be measured is constituted on the open surface. At present, therefore, the closed type cell and the open type cell are used depending upon the samples and the applications. Compared with the closed type photoacoustic cell, however, the open type photoacoustic cell is affected by the environmental noise and gives large noise components and low sensitivity. In order to decrease the effect of noise components there has been proposed a method (P. Poulet, J. Chambron, J. Photoacoustics, 1, 329–346 (1983)) which uses two photoacoustic cells, i.e., a cell of the measuring side which is irradiated with light and a cell of the reference side which is not irradiated with light but measures the noise components only, in order to detect the difference between the two signals using a differential microphone. However, the intensity of the photoacoustic signal detected by the cell of the measuring side has not been measured at a resonance frequency and is weak since the light signal is not strong. Moreover, light beams irradiating the cell of the measuring side and the cell of the reference side have different phases, the noise is not completely erased by the differential microphone, and the sensitivity is not improved.

In order to improve the intensity of the photoacoustic signal by bringing the modulation frequency of the irradiated light into agreement with the resonance frequency of the cell, furthermore, there has been reported a method (Kolmel, K.; Sennhenn, B.; Giese, K. J. Soc. Cosmet. Chem. 1986, 37, 375–385) which uses a resonance type cell of the measuring side and a cell of the reference side to make measurement after the noise has been removed by using a differential microphone. However, the cell of the measuring side and the cell of the reference side have different resonance frequencies and different noise components. Therefore, the difference is not perfect and good sensitivity is not obtained; i.e., it is desired to develop a more sensitive device.

There has further been disclosed in Japanese Unexamined Patent Publication (Kokai) No. 62-27215 a photoacoustic measuring device having an open type cell. According to this conventional photoacoustic measuring device constituted by a cell of the measuring side and a cell of the reference side, either one of the microphones is mounted by using a threaded block. The capacity of the cell is adjusted by the threaded block to control the resonance (Helmholtz's resonance) frequency of the cell.

Therefore, the above conventional device makes it possible to intensify the optimum signals at the resonance frequency.

Furthermore, use has heretofore been made of a xenon lamp or a deuterium lamp as a source of light for the photoacoustic measuring device, and the monochromatic light is obtained through a spectroscope and is guided to the photoacoustic cell through the light guide. Therefore, the light falling on the sample from the light guide has optical intensities at each of the wavelengths of the order of nW to μW, and the obtained photoacoustic signals are as weak as several tens of nV. In order to obtain these signals, a complex signal analyzing technology (signal analyzer, analytical software, or the like) is necessary.

However, the conventional photoacoustic (hereinafter referred to as PAS) measuring technology using the open type cell develops the following problems.

(1) Since the intensity of the source of light (particularly ultraviolet light) is weak, the obtained PAS signals are so small that the measurement is not obtained with a high sensitivity. That is, with the xenon lamp or the deuterium lamp used so far as the source of light, the intensity of light per a wavelength is small. A laser beam must be used.

(2) The conventional open type PAS cell has not been optimized in its constitution from the standpoint of amplifying the PAS signals or removing noise and further has a large dead volume (about 1 ml), making it difficult to obtain measurement with a high sensitivity. That is, the photoacoustic signal consists of a sound wave which changes with a change in the pressure and it is considered that the sensitivity increases with a decrease in the volume of the cell. With the conventional cell structure, however, it is difficult to decrease the dead volume. It is therefore urged to study the cell structure which minimizes the dead volume. This holds true even with the conventional closed type cell.

(3) In carrying out the analysis in the direction of depth, it is not allowed to optimize the sensitivity depending upon the conditions. That is, the data in the direction of depth is obtained by changing the frequency of photoacoustic measurement. In the case of the conventional photoacoustic cell, however, the sensitivity is simply improved at only one measuring frequency owing to the effect of resonance. To carry out the analysis in the direction of depth with a high sensitivity, therefore, it becomes necessary to use a photoacoustic cell having a structure that is capable of freely developing resonance at any frequency of measurement.

In recent years, furthermore, it has been demanded to provide a measuring device with high sensitivity and high accuracy in a variety of fields such as measuring the amount of moisture in human skin and measuring the percutaneous absorption of medicines. At present, however, a suitable device has not been developed.

As a method of evaluating the percutaneous absorption of medicines, for example, there has been proposed the in-vivo measuring method using an RI (radioisotope) or the like. This method, however, requires a complex measuring system and is cumbersome to use. Usually, therefore, the in-vitro measuring method has been put into practical use by employing a relatively simply constructed diffusion cell.

Though a variety of diffusion cell methods have been developed to bring the conditions closer to those of actual living tissue, it has still been strongly desired to develop simple in-vivo and in-vitro evaluation methods with a high sensitivity and high accuracy.

Furthermore, a variety of lasers have been developed as sources of light for use in infrared, visible, and ultraviolet regions having very greater output intensities than those of the generally used incoherent xenon lamps and deuterium lamps. Use of these lasers as a source of light for the photoacoustic measuring method makes it possible to achieve high sensitivity and high accuracy. Though there has not yet been provided an ultraviolet laser that continuously emits light in the ultraviolet region, it is possible to continuously emit ultraviolet light if a laser that continuously emit light such as argon laser or krypton laser is combined with a nonlinear optical crystal. This is expected to be widely adapted to medicines.

It is further considered to be effective in studying the percutaneous absorption of medicines based on the analysis in the direction of depth, which is a feature of the photoacoustic method.

Further, the closed type photoacoustic cell that is now generally used is a system in which a sample is introduced into a sample holder made of quartz and is hermetically closed in the cell, having a defect of a relatively great dead volume. If the dead volume can be decreased, the sensitivity is improved correspondingly. It is therefore necessary to study the constitution of a closed type cell having a small dead volume. It is further desired that the closed type cell can be easily used.

The conventional photoacoustic measuring device employs the closed type cell or the open type cell depending upon the object of measurement and, hence, two devices and systems therefor must be assembled each time. The range of application will spread greatly if there is available a photoacoustic measuring device equipped with a photoacoustic cell which can be easily switched to that of the closed type and that of the open type. It is therefore urgently desired to improve the photoacoustic measuring device.

SUMMARY OF THE INVENTION

The present invention was completed in view of the aforementioned problems inherent in the prior art and has as its object to provide a photoacoustic cell and a photoacoustic measuring device which make it possible to measure a sample in-vivo or in-situ at any place with a higher sensitivity and higher accuracy, as well as to obtain data in the direction of depth.

Another object of the present invention is to provide a photoacoustic cell which works both as the cell of the closed type and the cell of the open type equipped with a closed type cell that is highly sensitive, small in size, and easy to use, as well as a photoacoustic measuring device having the same cell.

In accordance with the present invention, there is provided a photoacoustic cell, comprising a light guide having a fiber portion consisting of a bundle of a number of optical fibers and a covering portion by which the side surface of said fiber portion is covered, said covering portion of the light guide extending beyond the fiber portion in a manner that when a first end of the light guide is brought into contact with the surface of a material to be measured, a closed space is defined by the end surface of the fiber portion, by the inner wall of the covering portion and by the surface of the material to be measured; a pipe having a first end that is open in the closed space and a second end that penetrates through the covering portion and is open toward the outside of the covering portion; and a microphone that is coupled to the second end of the pipe.

Preferably, the above pipe has at least one folded portion on the inside of the covering portion, the length of the extended portion of the covering portion is adjustable, and the length of the above pipe is adjustable.

Preferably, furthermore, provision is made of a sample holder which is detachably attached to the extended portion of the covering portion and, when it is attached, defines a closed space being defined by the end surface of the fiber portion and by the inner wall of the covering portion.

In accordance with the present invention there is also provided a photoacoustic measuring device, comprising the above-mentioned photoacoustic cell, a light supplying means for supplying a light beam whose light intensity is modulated with modulation signals of a predetermined frequency to the second end of the light guide, and a signal detecting means for detecting only those components that are in synchronization with the modulation signals out of the signals output from the microphone.

Preferably, the frequency of the modulation signals is changeable, and the light supplying means is comprised of a visible laser which outputs a laser beam of a visible region, a UV oscillation unit which outputs the laser beam after having converted the wavelength thereof into one-half, and a light chopper which shields the light in synchronization with the modulation signals.

In the photoacoustic cell of the present invention, the covering portion at an end of the light guide is protruded beyond the fiber portion and a closed space is formed relative to a portion that is to be measured. This closed space turns out to be a dead volume. Therefore, an open type cell which minimizes the dead volume is formed together with the light guide as a unitary structure. Since the length of the extended portion is adjustable, the dead volume is adjustable, too, and optimum sensitivity is obtained based on this adjustment.

The pipe that guides the generated acoustic signals from the closed space to the microphone on the outside of the light guide, has a folded portion and has a length that is adjustable. It is therefore allowed to adjust the resonance frequency and to optimize the sensitivity at any modulation frequency. By detachably providing the sample holder, furthermore, the cell can be used as either the open type one or the closed type one.

According to the photoacoustic measuring device using the photoacoustic cell of the present invention, furthermore, the modulation frequency is changed and the resonance frequency is adjusted to meet the same, making it possible to carry out the analysis in the direction of depth. Furthermore, use of a visible laser and a UV oscillation unit as a source of light makes it possible to obtain a sufficient degree of optical sensitivity.

DESCRIPTION OF THE PREFERRED EMBODIMENTS

A preferred embodiment of the present invention will now be described in conjunction with the drawings.

Figure 1:
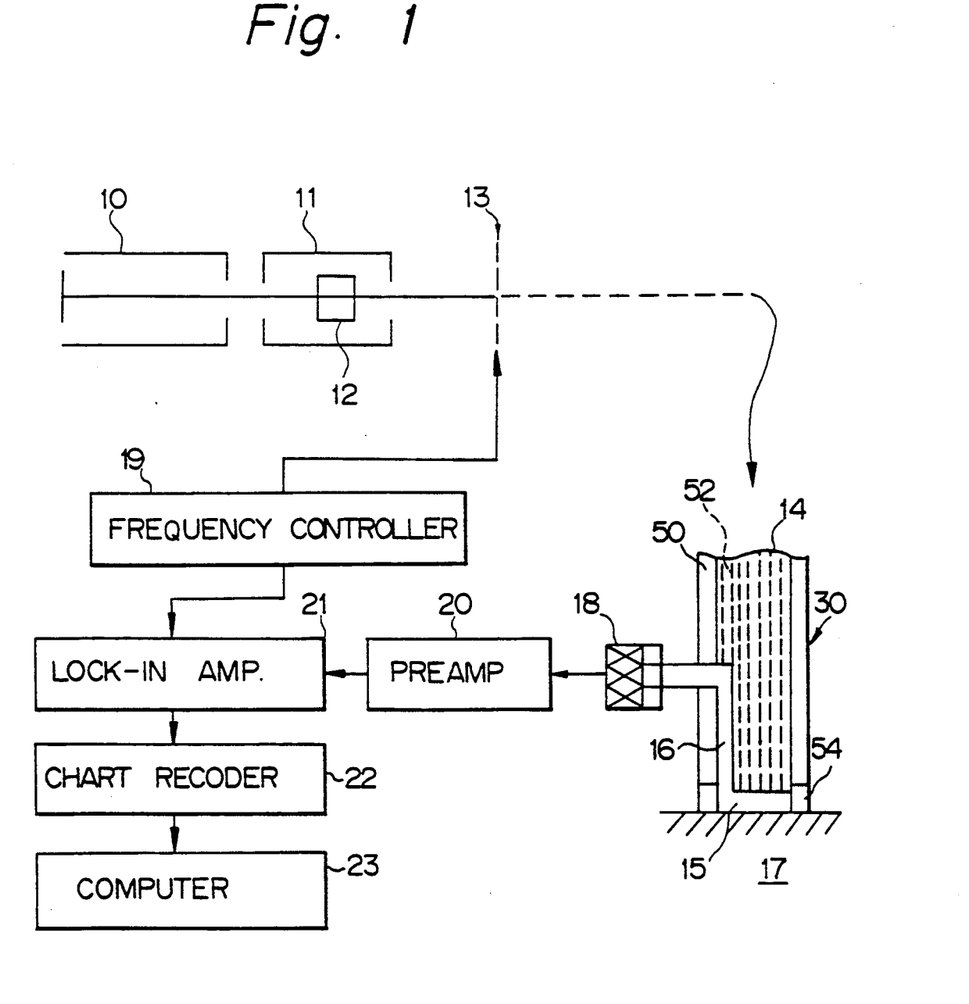
FIG. 1 is a diagram explaining the circuit constitution of a photoacoustic measuring device according to an embodiment of the present invention.

FIG. 1 shows a photoacoustic measuring device according to an embodiment of the present invention which is constituted by light source portions (10, 11, 12), modulating portions (13, 19), a photoacoustic cell portion 30, and processing portions (20, 21, 22, 23).

A UV laser beam is emitted from a light source which consists of an argon laser (visible laser) 10 incorporating a UV oscillation unit 11 that uses a nonlinear optical crystal (BBO) to convert the wavelength into one-half and is modulated through the optical chopper 13. The modulated UV light is guided to a light guide 14 and is allowed to fall on the surface of a sample 17. Here, the source of light 10 may be a krypton laser or a helium-cadmium laser provided it continuously emits light.

A feature of the present invention resides in that the light guide 14 directly serves as a photoacoustic sensor.

The photoacoustic cell portion 30 consists of the (bundled type) light guide 14, a sample chamber 15 having a volume of 10 to 50 $\mu$l formed between the end surface of the bundled fibers 52 and the surface of the sample 17, a pipe 16, and a microphone 18.

A portion 54 of the photoacoustic cell 30 that is pressed onto the sample is made of a light-transmitting material to reduce the background signals. In this embodiment, for instance, this portion 54 is made of a quartz glass over a distance of 2 mm from the tip of the cell.

The light guide 14 is covered by stainless steel as designated at 50.

A feature of the photoacoustic measuring device of the present invention resides in that the sample chamber is provided in the light guide 14 and is further coupled to a microphone chamber 18 through the folded pipe 16.

Further, a feature residues in that the pipe 16 has a length of 10 to 100 mm inside and outside the light guide, the length being adjustable depending upon the measuring conditions. Typically, the pipe has a total length of 8 cm, the length of the pipe being 5 cm inside the light guide and being 3 cm outside the light guide.

In the past, a gas was sealed inside the cell to improve the sensitivity, but this presents a problem in using the cell, and it is physically impossible to completely seal the gas inside the cell.

According to this embodiment, therefore, a resonance frequency specific to the cell is measured by developing Helmholtz's resonance at a high frequency (2 kHz or higher) that is not strongly affected by the environmental noise by utilizing the half-sealed condition of gas in the cell. In this embodiment, a resonance frequency of 2.2 kHz is exhibited when the pipe has a total length of 8 cm. Therefore, the signals become maximum when the modulation signals have the above frequency.

A signal detected by the photoacoustic cell is amplified through a preamplifier 20 and is input to a lock-in amplifier 21 which takes out from the signals the same frequency component only as the modulation frequency of the irradiated light generated by a frequency controller 19. The frequency component taken out is then recorded onto a chart recorder 22 and is analyzed by a computer 23.

Here, the data of the sample in the direction of depth can be obtained by changing the modulation frequency. That is, the length of thermal diffusion decreases with an increase in the modulation frequency making it possible to obtain data on the surface, and the length of thermal diffusion increases with a decrease in the modulation frequency making it possible to obtain data from the interior.

According to the thus constituted photoacoustic measuring device of the present invention, the surface of the sample is irradiated with the light and sound waves generated due to heat as the light is absorbed by the surface of the sample. The sound waves from the sample that absorbs the light are amplified owing to the effect of resonance, while the photoacoustic signals are little affected by the environmental noise owing to the folded pipe. The photoacoustic measuring apparatus of the present invention has a photoacoustic cell that is formed together with the light guide as a unitary structure and has a small dead volume. Moreover, provision of the folded pipe that optimizes the effect of resonance makes it possible to improve the sensitivity by more than one order compared with that of the conventional cells.

When the analysis is carried out in the direction of depth by changing the frequency, the conventional PAS cell exhibits improved sensitivity at only one frequency of resonance. According to the present invention, on the other hand, the resonance takes place at any frequency making it possible to optimize the frequency.

Figure 2:
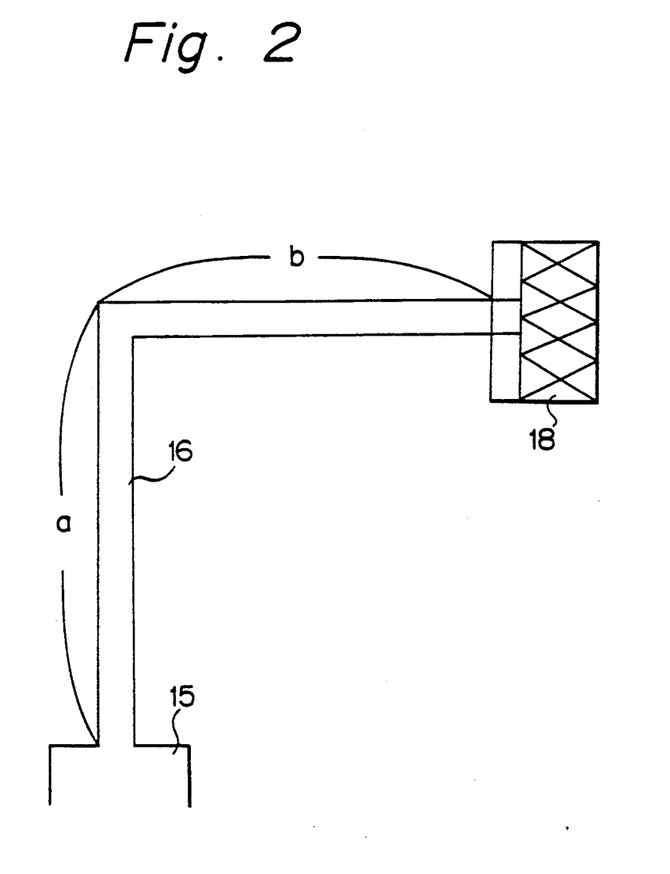
FIG. 2 is a diagram explaining the relationship between folding the pipe and the resonance frequency.

The resonance frequency and sensitivity of the PAS cell, which is a chief component of the photoacoustic measuring device of the present invention, are determined by the following dimensions:

That is, the resonance frequency is determined by the length of the pipe. When the length a is fixed and the length b is varied as shown in FIG. 2, then the resonance frequency is expressed by the following relationship:

$$f = mc/(2L)$$

f: resonance frequency,
m: natural number,
c: speed of sound,
L: length of the pipe, (fundamental resonance frequency when m=1).
When the length a is changed, $$f = Rmc/(2L)$$

f: resonance frequency,
m: natural number,
c: speed of sound,
L: length of the pipe, R: acoustic constant specific to a, (fundamental resonance frequency when m=1).

The sensitivity is determined by the volume (V) of the sample chamber and the folded degree of the pipe. Under adiabatic conditions, the product of the pressure (P) times the volume (V) of the sample chamber is constant. Therefore, the sensitivity increases with the decrease in the volume (photoacoustic signal consists of sound wave that varies accompanying a change in the pressure). However, generation of sound is affected if the volume becomes too small. The volume should preferably be from 10 to 50 $\mu l$ and more preferably from 35 to 45 $\mu l$.

As for the sensitivity by the folded degree of the pipe having L=8, the greatest value is exhibited when a=4 and b=4, and the smallest value is exhibited when a=5 and b=3.

Figure 3:
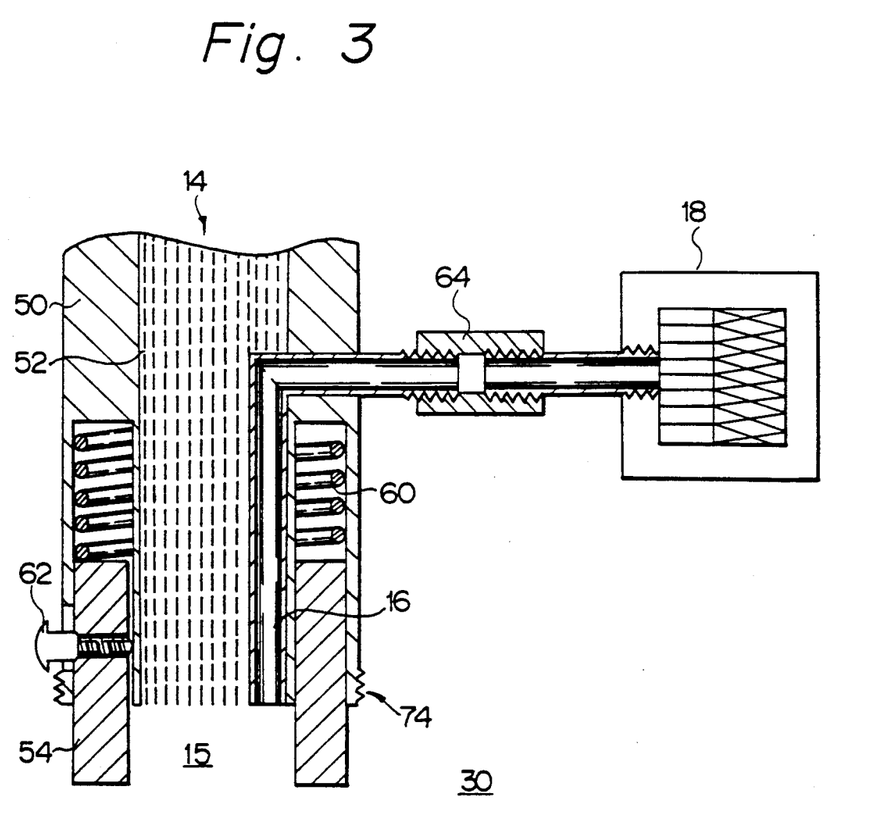
FIG. 3 is a sectional view of a photoacoustic cell according to the embodiment of the present invention.

FIG. 3 is a sectional view which shows in further detail the constitution of the photoacoustic cell 30 shown in FIG. 1.

In the end of a stainless steel covering 50 which covers the periphery of the bundled fiber 52 of the light guide 14, a circular groove is formed to accept a cylinder 54 made of quartz glass. The cylinder 54 is urged by a spring 60 toward the direction in which it is to be pushed out and is secured by a screw 62. The screw 62 is loosened to push the cylinder 54 into a desired depth and is then tightened thereby to adjust the volume of the sample chamber 15. Further, the pipe 16 is connected together at its intermediate portion by screwing a pipe 64 that has a larger outer diameter; i.e., by adjusting the screwing amount, the length of the pipe 16 can be adjusted. The sample holder 70 is internally threaded as designated at 72 and engages with a thread 74 formed on the stainless steel covering 50 to form a closed space which can then be used as the closed type cell. A portion 76 forming the closed space of the sample holder 70 is composed of quartz glass in order to reduce the background signals. The volume of the sample chamber 15 can also be adjusted by adjusting the screwing amount of the sample holder 70. Described below are examples of actual measurement.

EXAMPLE 1

Figure 4:
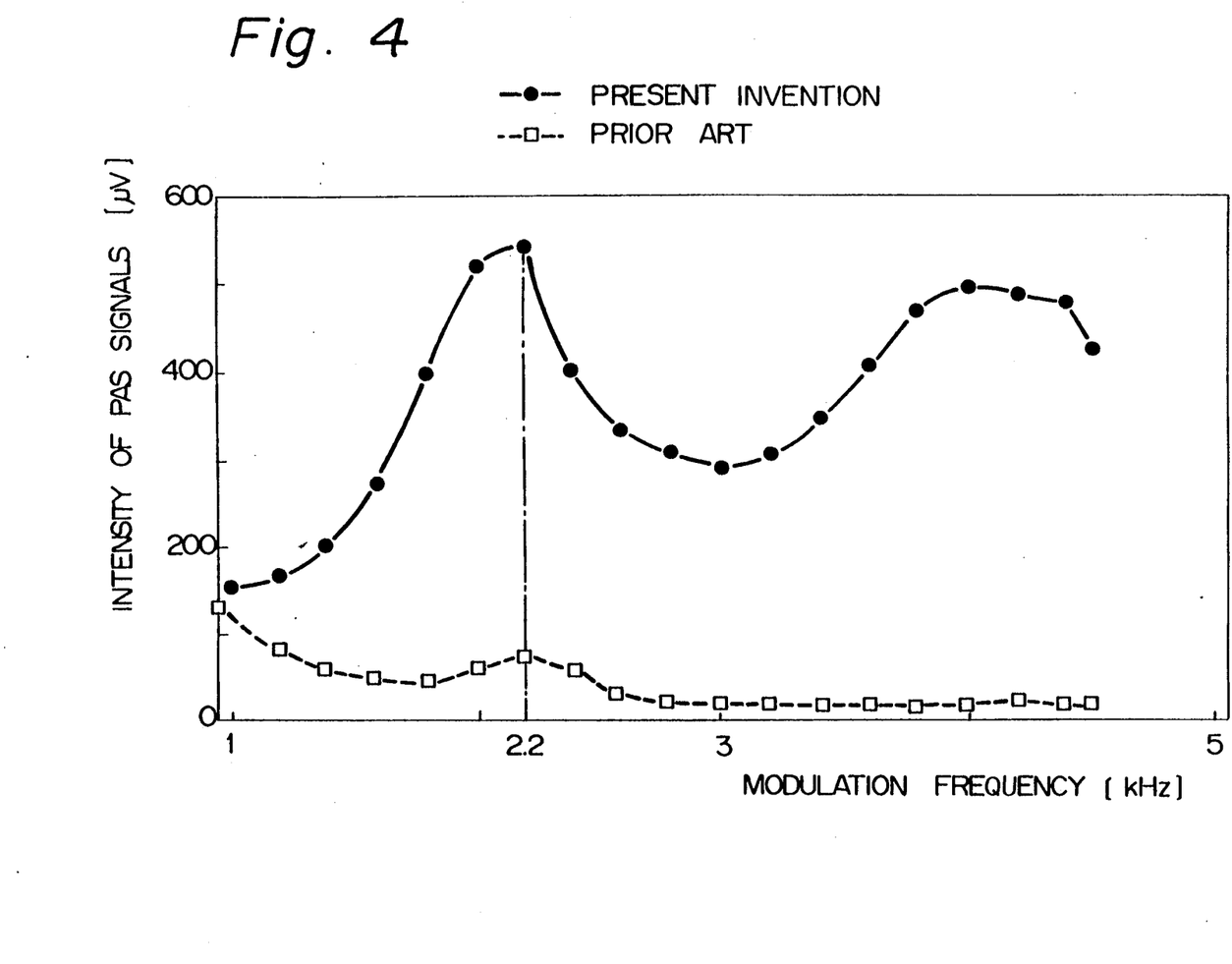
FIG. 4 is a diagram comparing the sensitivity of the cell for a UV photoacoustic measuring device using a cell formed together with the UV light guide as a unitary structure of the present invention with the sensitivity of the conventional cell for the visible light-acoustic measuring device.

Comparison of sensitivity of cell of conventional system with sensitivity of cell of invention Sample: Black rubber
Measuring frequency: 1 to 4.5 kHz
Wavelength of light source: 488 nm (visible light)
Intensity of the light: 3 mW FIG. 4 shows the intensities of PAS signals measured at various modulation frequencies by using the cell of the conventional system and the cell of the present invention. The cell of the present invention is adjusted to exhibit a maximum sensitivity at 2.2 kHz. It will be understood that at around 2.2 kHz, the cell of the present invention produces signals of a sensitivity which is sufficiently higher than that of the cell of the conventional system. This frequency is very far from the frequencies of environmental noises, and the effect thereof can be fully eliminated.

EXAMPLE 2

Measuring accuracy of invention for indometacin ointment and qualitative property Model sample: Indometacin ointment
Base agent: PEG (polyethylene glycol)

Figure 5:
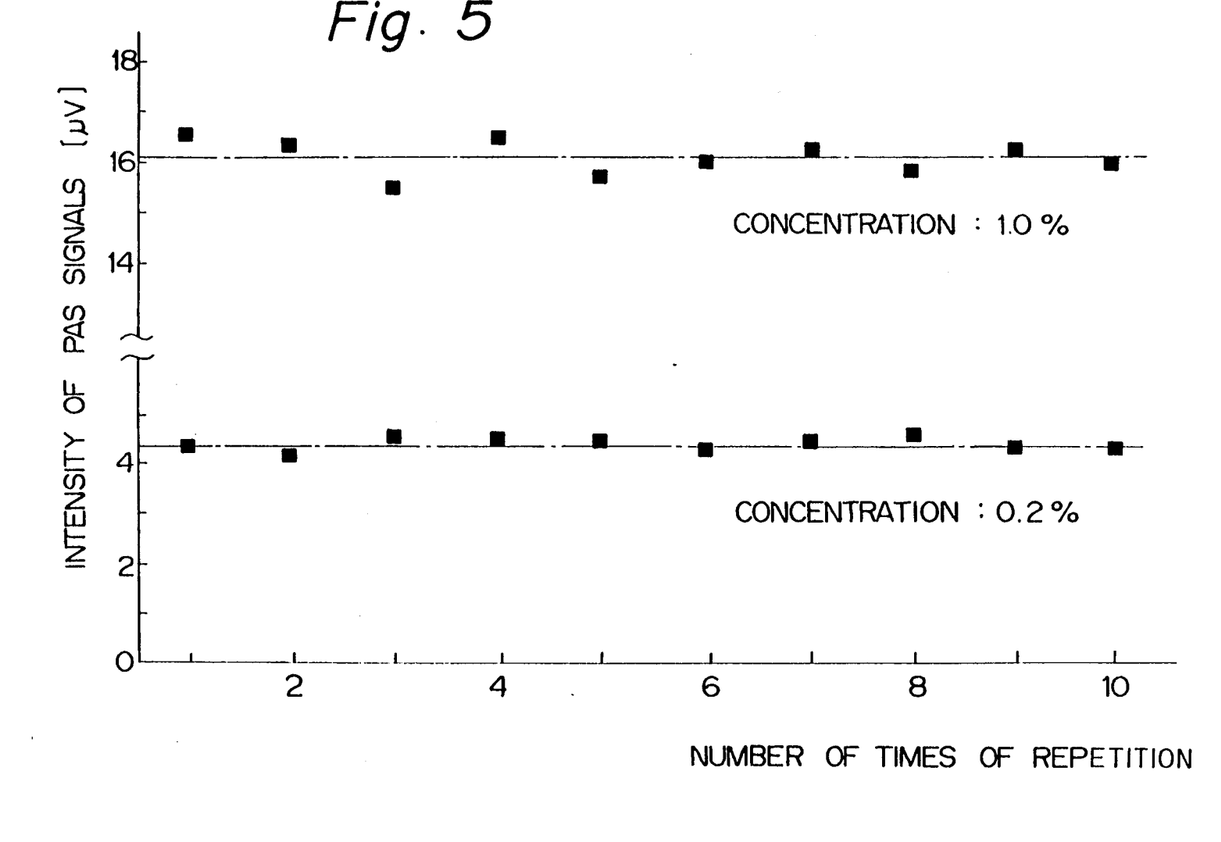
FIG. 5 is a diagram explaining the measuring accuracy of the photoacoustic measuring device of the present invention.

Measuring frequency: 2.2 kHz
Wavelength of light source: 257.2 nm
Intensity of light: 3 mW FIG. 5 shows the measuring accuracy when the measurement is taken repetitively 10 times. The degree of change is 3.0% at a concentration of 0.2% and is 2.0% at a concentration of 1.0%, providing excellent accuracy.

Figure 6:
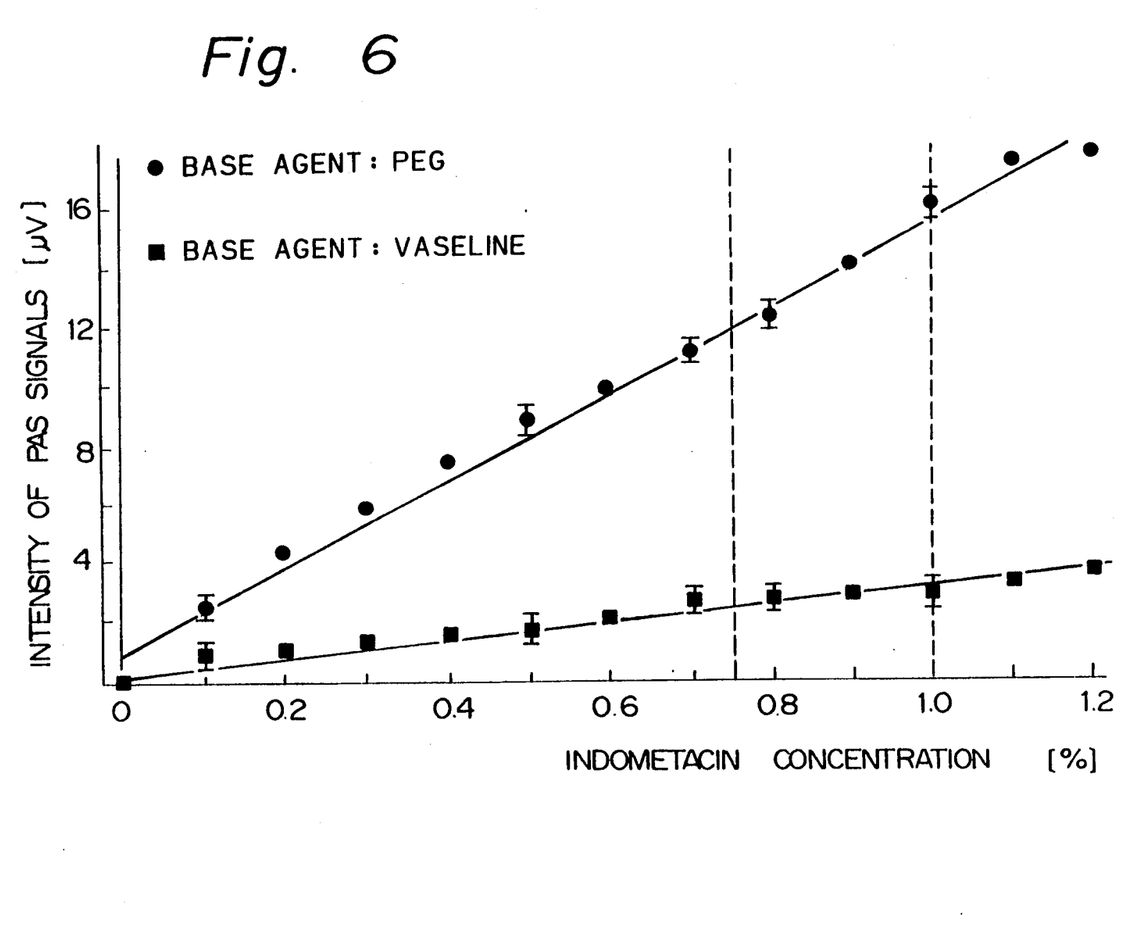
FIG. 6 is a diagram showing calibration curves of an indometacin ointment (base agents: polyethylene glycol and vaseline)

FIG. 6 shows calibration curves of indometacin. Excellent quantitative properties, i.e., coefficients of correlation of 0.996 and 0.984, are exhibited in the base agents of PEG and vaseline at a concentration of 0 to 1.2%. In the drawing, the values of 0.75% and 1.0% indicated by broken lines represent concentrations adapted to general customer's use and medical practitioner's use. The drawing shows utilizability to a sufficient degree over this region.

EXAMPLE 3

In-vivo test for measuring percutaneous absorption
Device: UV-PAS measuring device
Sample: 1% indometacin ointment (base agent: PEG)

Figure 7:
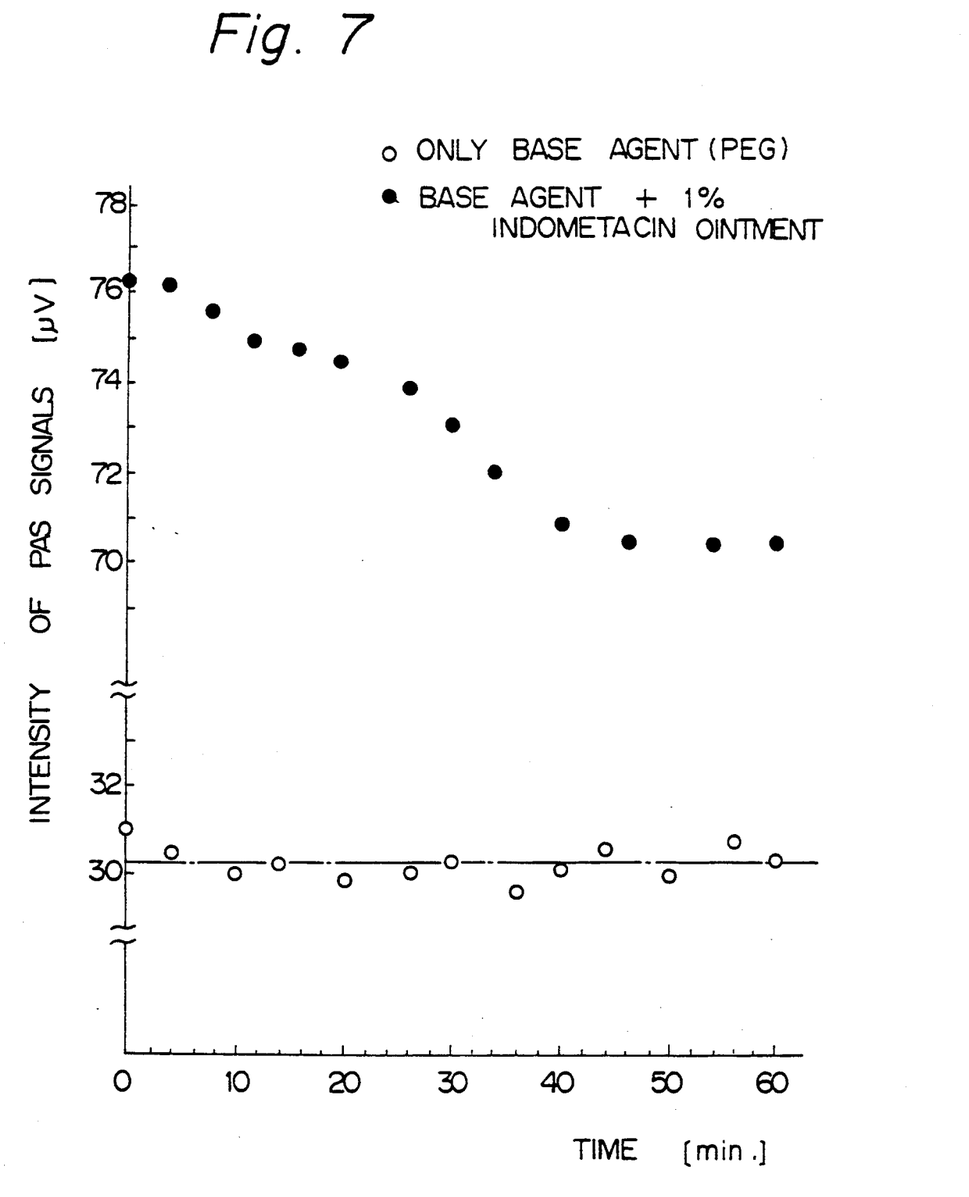
FIG. 7 is a diagram showing in-vivo percutaneous absorption measured by using the photoacoustic measuring device of the present invention.
Figure 8:
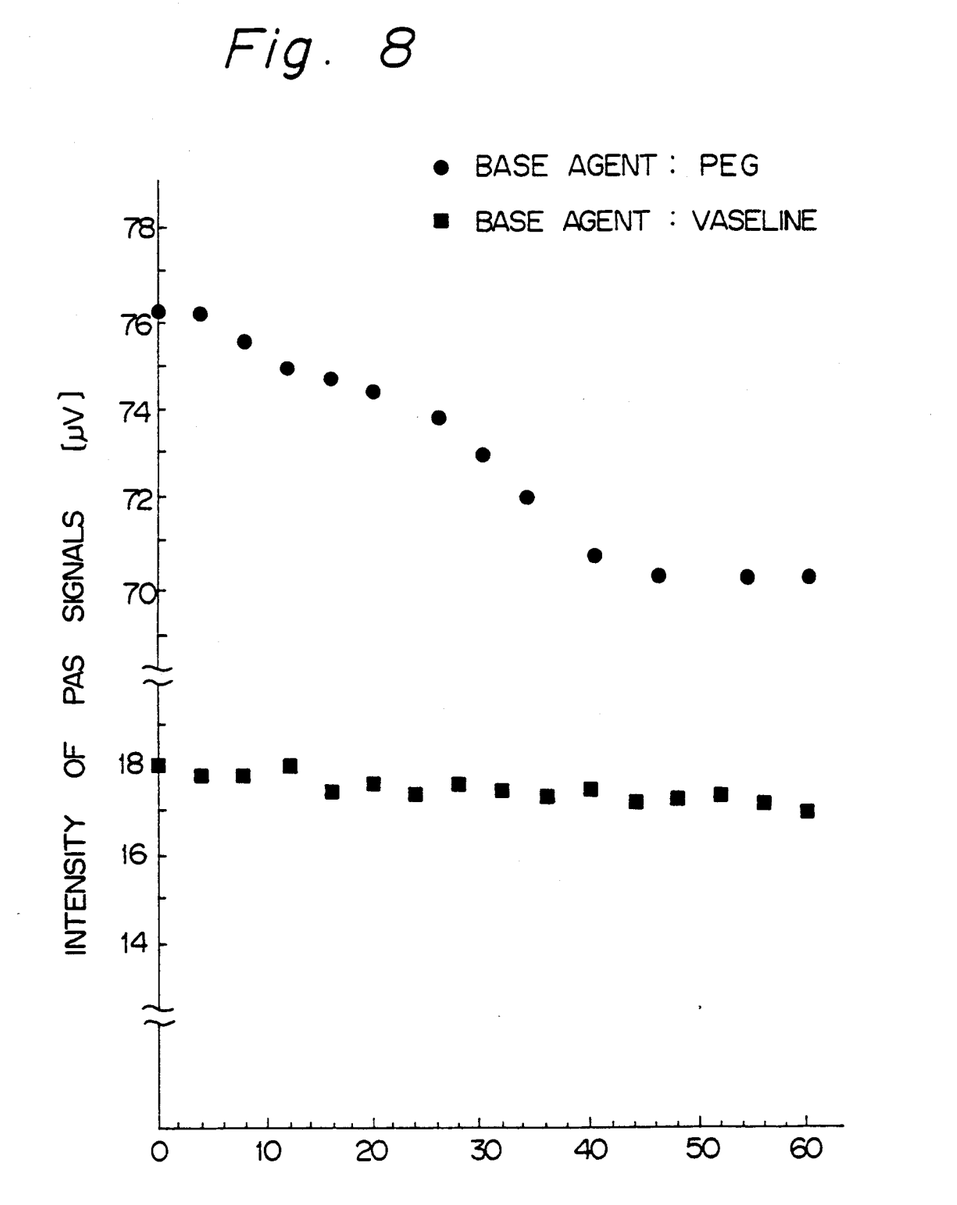
FIG. 8 is a diagram showing in comparison the in-vivo percutaneous absorption by base agents by using the photoacoustic measuring device of the present invention.

The results are shown in FIGS. 7 and 8. When the base agent only is applied, as will be understood from FIG. 7, the PAS signals exhibit a constant value but when the indometacin ointment is applied, the PAS signals become weak. Thus, the photoacoustic device of the present invention clearly indicates the degree of percutaneous absorption of the medicine. Further, FIG. 8 indicates the difference in the percutaneous absorption depending upon the base agents, i.e., indicates the fact that better percutaneous absorption is obtained when PEG is used than when vaseline is used, from which it will be understood that the photoacoustic measuring device of the present invention exhibits good accuracy and sensitivity.

The photoacoustic measuring device of the present invention which is constructed as described above offers the following effects.

That is, the photoacoustic cell which is formed together with the light guide as a unitary structure has a small dead volume, contributing to improving the sensitivity by more than one order compared to that of the conventional cell, together with the provision of the folded pipe, which is intended to optimize the effect of resonance.

In carrying out the analysis in the direction of depth by arbitrarily changing the frequency, the conventional PAS cell exhibits improved sensitivity only at one frequency of resonance. The present invention, on the other hand, permits resonance to take place at any frequency enabling the sensitivity to be optimized.

Moreover, either the open type or the closed type system can be used depending upon the sample and the measurement can be made with optimum sensitivity.

Therefore, the photoacoustic measuring device of the present invention is expected to be used as a highly sensitive and highly accurate measuring device required in the fields of measuring the amount of moisture in human skin and measuring the percutaneous absorption of medicines. Furthermore, even when used as a closed type cell, the device is smaller in size and is easier to use than that of the conventional type and is expected to be widely used as a photoacoustic cell.

We claim:

1. A photoacoustic cell, comprising:
a light guide having a fiber portion consisting of a bundle of a number of optical fibers and a covering portion by which the side surface of said fiber portion is covered, said covering portion of said light guide extending beyond said fiber portion in a manner that when a first end of said light guide is brought into contact with the surface of a material to be measured, a closed space is defined by the end surface of said fiber portion, by the inner wall of said covering portion, and by the surface of said material to be measured;
a pipe having a first end that is open in said closed space and a second end that penetrates through said covering portion and is open toward the outside of said covering portion; and
a microphone that is coupled to the second end of said pipe.

2. A photoacoustic cell according to claim 1, wherein said pipe has at least one folded portion on the inside of said covering portion.

3. A photoacoustic cell according to claim 1, wherein said covering portion has adjusting means for adjusting the length of the extended portion of said covering portion.

4. A photoacoustic cell according to claim 1, wherein said pipe has adjusting means for adjusting the length of said pipe.

5. A photoacoustic cell according to claim 1, further comprising a sample holder which is detachably attached to the extended portion of said covering portion and, when it is attached, defines a closed space with the end surface of said fiber portion and the inner wall of said covering portion.

6. A photoacoustic measuring device, comprising:
a photoacoustic cell comprising a light guide having a fiber portion consisting of a bundle of a number of optical fibers and a covering portion by which the side surface of said fiber portion is covered, said covering portion of said light guide extending beyond said fiber portion in a manner that when a first end of said light guide is brought into contact with the surface of a material to be measured, a closed space is defined by the end surface of said fiber portion, by the inner wall of said covering portion, and by the surface of said material to be measured, a pipe having a first end that is open in said closed space and a second end that penetrates through said covering portion and is open toward the outside of said covering portion, and a microphone that is coupled to the second end of said pipe;
a light supplying means for supplying a light beam whose light intensity is modulated with modulation signals of a predetermined frequency to the second end of said light guide; and
a signal detecting means for detecting only those components that are in synchronization with said modulation signals out of the signals output from said microphone.

7. A photoacoustic measuring device according to claim 6, wherein the frequency of said modulation signals is changeable.

8. A photoacoustic measuring device according to claim 6, wherein said pipe has at least one folded portion on the inside of said covering portion.

9. A photoacoustic measuring device according to claim 6, wherein said covering portion has adjusting means for adjusting the length of the extended portion of said covering portion.

10. A photoacoustic measuring device according to claim 6, wherein said pipe has adjusting means for adjusting the length of said pipe.

11. A photoacoustic measuring device according to claim 6, further comprising a sample holder which is detachably attached to the extended portion of said covering portion and, when it is attached, defines a closed space with the end surface of said fiber portion and the inner wall of said covering portion.

12. A photoacoustic measuring device according to claim 6, wherein said light supplying means include a visible laser which outputs a laser beam of a visible region, a UV oscillation unit which outputs the laser beam after having converted the wavelength thereof into one-half, and a light chopper which shields the light in synchronization with said modulation signals.

* * * * *